United States Patent
Azzi (12)

(10) Patent No.: US 6,350,776 B1
(45) Date of Patent: Feb. 26, 2002

(54) METHOD OF TREATING PROLIFERATIVE DISEASE WITH LYCOPENE AND ALPHA-TOCOPHEROL

(76) Inventor: Angelo Manfredo Azzi, Luisenstrasse 46, Berne CH-3005 (CH)

( * ) Notice: Subject to any disclaimer, the term of this patent is extended or adjusted under 35 U.S.C. 154(b) by 0 days.

(21) Appl. No.: 09/665,937

(22) Filed: Sep. 20, 2000

Related U.S. Application Data

(60) Provisional application No. 60/154,774, filed on Sep. 20, 1999.

(51) Int. Cl.$^7$ ........................ A61K 31/355; A61K 31/01
(52) U.S. Cl. ........................... 514/458; 514/762
(58) Field of Search ................... 514/458, 762

(56) References Cited

FOREIGN PATENT DOCUMENTS

| NL | 7400862 | * | 7/1975 |
| WO | WO 96/19215 | | 6/1996 |
| WO | WO 96/19217 | | 6/1996 |

OTHER PUBLICATIONS

Wang et al, J. Cell. Biochem., 62(1), pp 19–26 Abstract Only, 1996.*
Sharoni et al, Spec. Publ.–R. Soc. Chem., pp 378–385, Abstract Only 1996.*
Giovannucci and Clinton, 1998, "Tomatoes, lycopene, and prostate cancer", Proc. Soc. Exp. Biol. Med. 218(2):129–39.
Heinonen et al., 1998, "Prostate cancer and supplementation with alpha–tocopherol and beta–carotene: incidence and mortality in a controlled trial", J. Natl. Cancer. Inst. 90(6):440–6.
Pastori et al., 1998, "Lycopene in association with α–tocopherol inhibits at physiological concentrations proliferation of prostate carcinoma cells", Biochem. Biophys. Res. Comm. 250:582–5.
Sharoni and Levy, 1996, "Anticarcinogenic properties of lycopene", Spec. Publ. R Soc. Chem. 181:378–85.
Sigounas et al., 1997, "dl–α–tocopherol induces apoptosis in erythroleukemia, prostate, and breast cancer cells", Nutr. Cancer 28(1):30–5.
Tasinato et al., 1995, "D–alpha–tocopherol inhibition of vascular smooth muscle cell proliferation occurs at physiological concentrations, correlates with protein kinase C inhibition, and is independent of its antioxidant properties", Proc. Natl. Acad. Sci. 92(26):12190–4.
Upston et al., 1999, "Tocopherol–mediated peroxidation of lipoproteins: implications for vitamin E as a potential anti-atherogenic supplement", FASEB J. 13(9):977–94.
Wang et al., 1996, "Reproducibility of erythocyte polyamine measurements and correlation with plasma micronutrients in an antioxidant vitamin intervention study", J. Cell. Biochem. 62(1):19–26.

* cited by examiner

*Primary Examiner*—Jerome D. Goldberg
(74) *Attorney, Agent, or Firm*—Pennie & Edmonds LLP

(57) ABSTRACT

A method of treating, inhibiting, or preventing proliferative disease, particularly cancer, by administering an effective amount of the combination of lycopene and alpha-tocopherol.

15 Claims, 3 Drawing Sheets

METHOD OF TREATING PROLIFERATIVE DISEASE WITH LYCOPENE AND ALPHA-TOCOPHEROL

Figure 1:
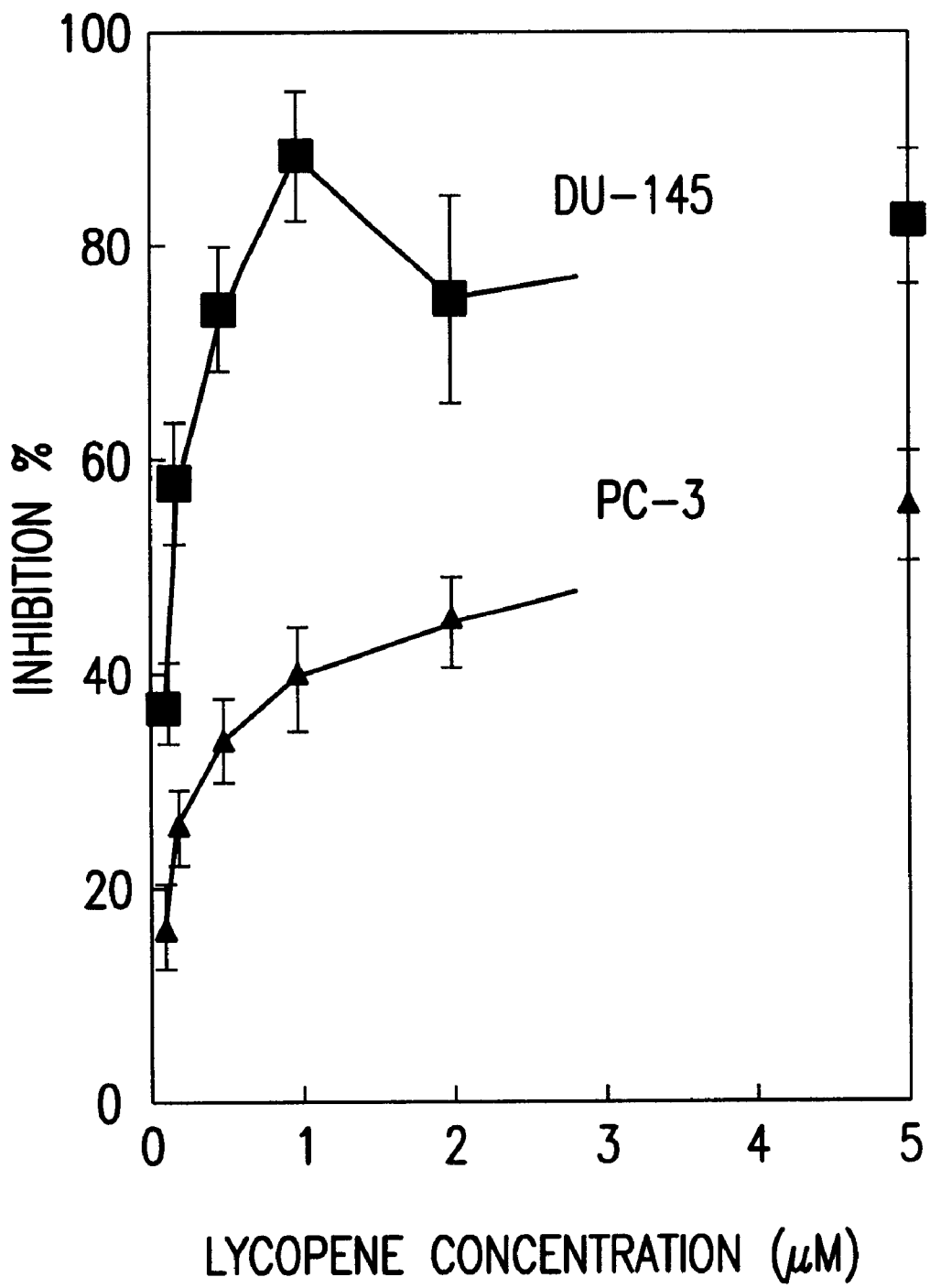

This application claims the benefit of provisional application No. 60/154,774, filed Sep. 20, 1999, which is hereby incorporated by reference in its entirety.

1. INTRODUCTION

The present application relates to methods of treating or preventing proliferative disease, particularly cancer, by administering to a subject a composition comprising lycopene and alpha-tocopherol.

2. BACKGROUND OF THE INVENTION

Lycopene, a natural red carotenoid found in nature in high amounts in tomatoes and also in tomato-derived products, is a potent antioxidant and free radical quencher. Lycopene has been found concentrated in various body tissues, such as liver, adrenal, and adipose tissues, as well as in the prostate. In vitro studies have shown that lycopene has a growth inhibitory effect on mammary, lung, and endometrial carcinoma cell proliferation at and an inhibitory effect on prostate carcinoma cell proliferation at concentrations of 50 $\mu$M and above. Little physiological significance can be attributed to the latter finding as the inhibitory concentrations in vitro far exceeded typical physiological plasma concentrations for lycopene. Epidemiological studies have associated lycopene intake with a decreased risk of prostate cancer.

Tocopherol compounds, also called vitamin E, are active components in vegetable oils. Vitamin E activity refers to the physiological activity of this group of nutrient materials. Materials having a vitamin E activity all belong to a distinct series of compounds which are all derivatives of chroman-6-ol. These compounds are all tocol derivatives having an isoprenoid C16-sidechain. The term "tocol" is used to mean 2-methyl-2-(4',8',12'-trimethyltridecyl) chroman-6-ol. These compounds are alpha-, beta-, gamma-, and delta-tocopherol, and are of primary importance for vitamin E activity.

Alpha-tocopherol is produced commercially for use as a feed supplement for domestic animals as a source of Vitamin E activity and as a nutrient supplement for humans. Tocopherols are also used in food technology as an antioxidant to retard the development of rancidity in fatty materials. The tocopherols are found widely distributed in normal foods, occurring in the highest concentration in the cereal grain oils, principally in corn and wheat oils, but also in barley and rye oils. They are also found in other vegetable oils such as safflower, soybean, peanut, cottonseed, linseed, sunflower, rapeseed and palm, and in other vegetable sources, e.g., palm leaves, lettuce, alfalfa, rubber latex and a variety of other plant materials. The proportion of the most active form, the D-alpha-tocopherol, varies widely among the different sources. Two sources having the highest levels of D-alpha-tocopherol are safflower oil and sunflower oil, although the most commonly available source is soybean oil, which has a considerably lower percent of D-alpha-tocopherol than safflower and sunflower oils, and with significantly higher percentages of the gamma- and delta-homologues. In addition to being a source for tocopherol homologues, palm oil, oats, rye, and barley also contain tocotrienol.

Of the tocopherols, alpha-tocopherol has the highest vitamin E activity and is the most valuable. Biochemical studies have shown that alpha-tocopherol inhibits cell proliferation in certain sensitive cell lines. Epidemiological studies also have associated alpha-tocopherol intake with a decreased risk of prostate cancer.

3. SUMMARY OF THE INVENTION

The present invention is based upon the discovery that lycopene and alpha-tocopherol synergize to inhibit cancer cell proliferation, that is, the combination of lycopene and alpha-tocopherol inhibits cancer cell proliferation to a greater extent than the additive inhibitory effects of lycopene and alpha-tocopherol alone on cancer cell proliferation.

Accordingly, the present invention provides methods of treating or preventing proliferative disease, particularly cancer, in a subject in need thereof, preferably a human subject, by administration of a composition comprising both lycopene and alpha-tocopherol. The composition containing lycopene and alpha-tocopherol is preferably administered so as to result in plasma levels of 0.01 to 5.0 $\mu$M lycopene and 1 to 100 4$\mu$M alpha-tocopherol.

4. BRIEF DESCRIPTION OF THE DRAWINGS

FIG. 1 depicts percent inhibition as a function of lycopene concentration on proliferation of human prostate carcinoma DU-145 and PC-3 cells treated with lycopene at the indicated concentrations and 50 $\mu$M alpha-tocopherol.

Figure 2A:
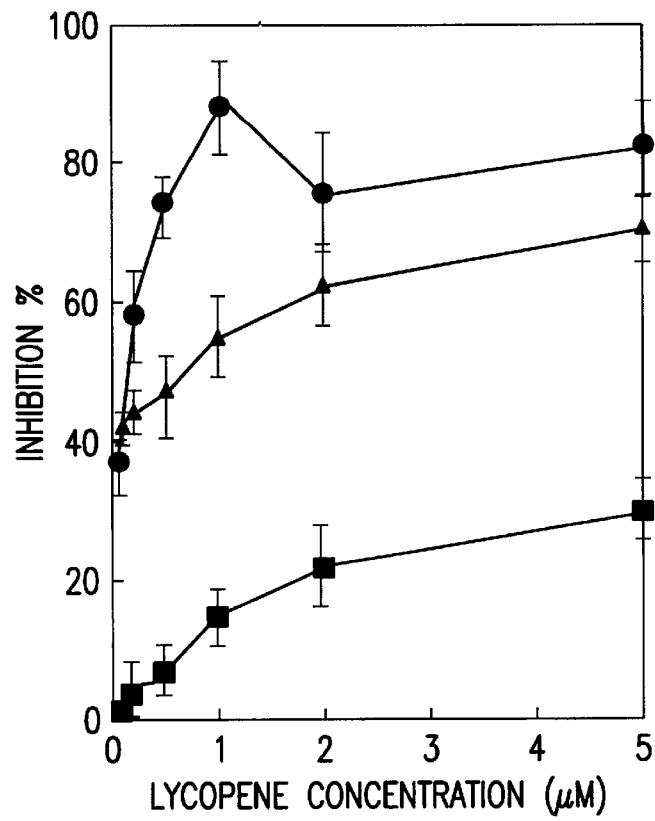

FIG. 2A depicts percent inhibition as a function of lycopene concentration on proliferation of human prostate carcinoma DU-145 cells treated with lycopene alone (square symbols) and with lycopene at the stated concentrations and 50 $\mu$M alpha-tocopherol (calculated (additive value of percent inhibition with lycopene at that concentration alone plus percent inhibition with 50 $\mu$M alpha-tocopherol alone) and experimentally obtained; triangle and circle symbols, respectively).

Figure 2B:
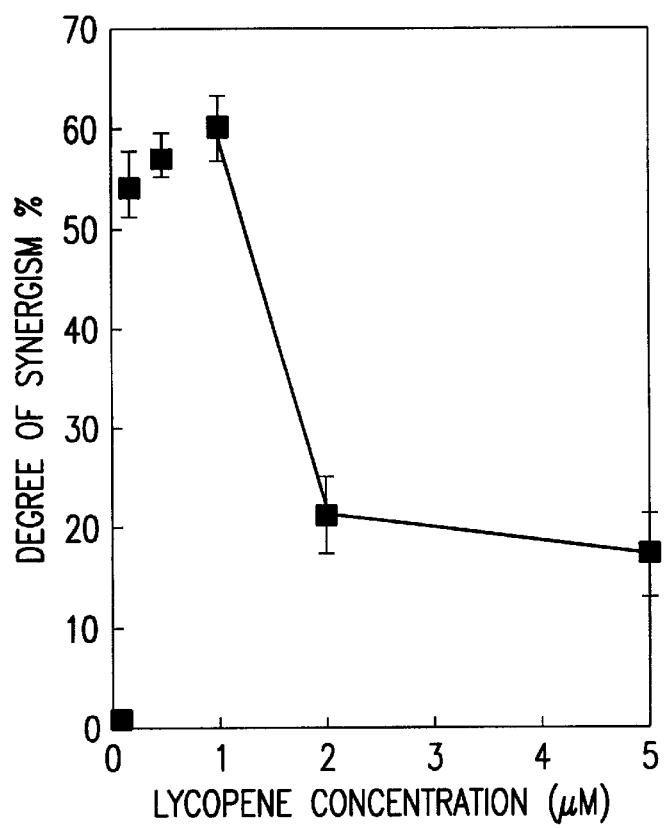

FIG. 2B depicts the degree of synergism (the difference between the actual percent inhibition obtained and the expected, additive level of inhibition with no synergism) as a function of lycopene concentration on proliferation of human prostate carcinoma DU-145 cells treated with lycopene at the stated concentrations and 50 $\mu$M alpha-tocopherol.

Figure 3A:
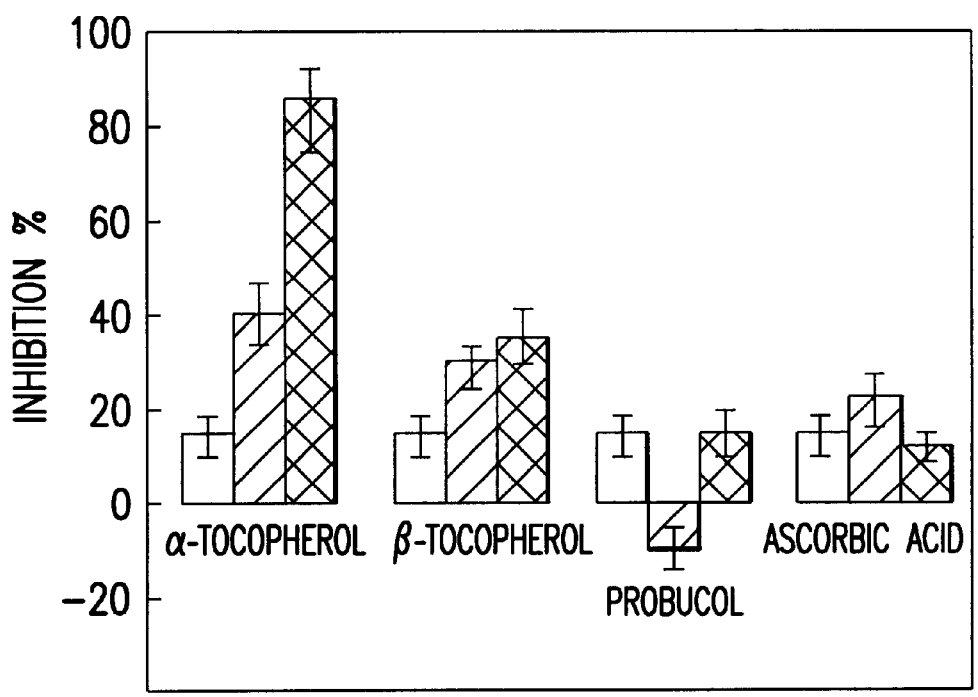

FIG. 3A depicts the relative inhibitory effect of alpha-tocopherol and other antioxidants each in combination with lycopene on the proliferation of human prostate carcinoma DU-145 cells. Open bars represent treatment with 1 $\mu$M lycopene alone, hatched bars represent treatment with 50 $\mu$M of the indicated compound, and cross-hatched bars indicate treatment with 1 $\mu$M lycopene and 50 $\mu$M of the indicated compound.

Figure 3B:
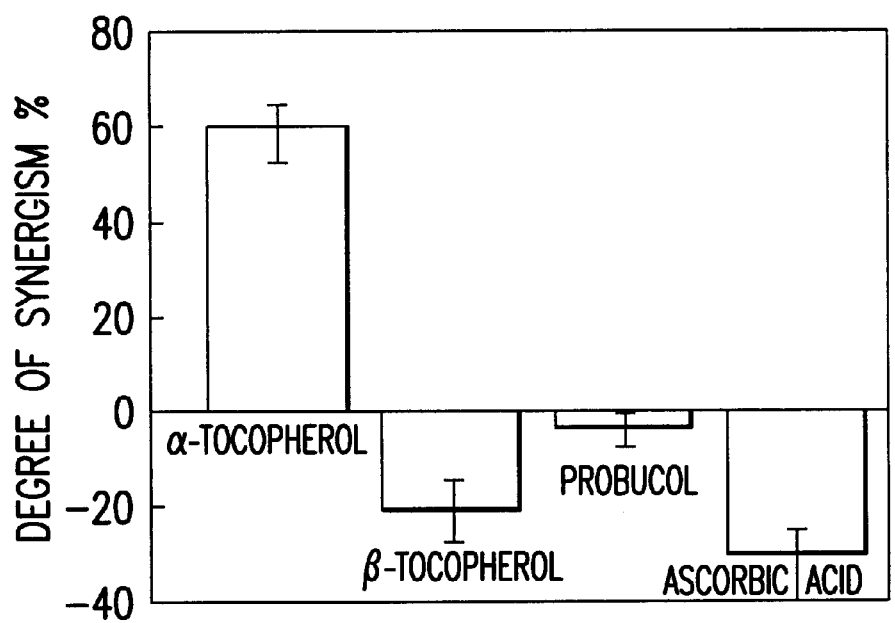

FIG. 3B depicts the relative synergism of 50 $\mu$M alpha-tocopherol and other antioxidants each in combination with 1 $\mu$M lycopene on the proliferation of human prostate carcinoma DU-145 cells.

5. DETAILED DESCRIPTION OF THE INVENTION

The present invention is based on the discovery that the combination of lycopene and alpha-tocopherol at low concentrations unexpectedly and synergistically inhibits the growth and proliferation of cancerous cells compared the additive inhibition of lycopene alone and alpha-tocopherol alone. According to the invention, therefore, a method of treating, inhibiting, or preventing proliferative disease, in particular cancer, is provided, wherein an amount of a composition comprising both lycopene and alpha-tocopherol effective to treat, inhibit, or prevent such disease is administered to a mammal, such as a human, in need of such treatment, inhibition, or prevention.

The amount of each active substance administered to the subject can and will vary according to the rates of absorption, bioavailability, etc., peculiar to the subject and the amount and administration route necessary to treat or prevent cancer and/or to achieve a target plasma concentration can be determined by methods known in the art. According to the invention, the amounts of lycopene and alpha-tocopherol administered in combination generally should result in a lycopene plasma concentration of 0.01 to 5.0 $\mu$M, preferably 0.1 to 1.0 $\mu$M, and more preferably 0.1 to 0.75 $\mu$M, and in an alpha-tocopherol plasma concentration of 1 to 100 $\mu$M, preferably 10 to 100 $\mu$M, and more preferably 25 to 75 $\mu$M.

The preferred mode for carrying out the method of the invention is by oral administration of compositions comprising lycopene and alpha-tocopherol, which can be prepared by conventional procedures known in the pharmaceutical and health supplement arts. Typically the active substances are mixed with physiologically acceptable and nontoxic carriers, diluents, excipients, stabilizers, or the like to form a liquid, semisolid, or solid form acceptable for oral administration. Suitable formulations and formulation techniques are disclosed in *Remington's Pharmaceutical Sciences,* 18th ed. (1990). Other methods of preparing formulations of carotenoids or tocopherols suitable for oral administration are disclosed in U.S. Pat. Nos. 5,891,907; 5,834,044; 5,827,539; 5,744,161; 5,643,623; 5,536,506; 5,221,735; and 5,180,747, the entire disclosures of which are incorporated herein by reference.

In specific embodiments, the lycopene-alpha-tocopherol compositions of the invention are administered to a mammal, preferably a human, that is susceptible to proliferative disease, for example, by genetic predisposition, exposure to environmental carcinogens, etc., to prevent or reduce the incidence of proliferative disease, e.g, cancer. In a preferred embodiment, the subject is predisposed to prostate cancer.

In a preferred mode, the active substances, i.e., lycopene and alpha-tocopherol, are suspended in an edible oil, such as soybean oil, corn oil, or any other edible triglyceride. The suspension may be formulated with surfactants, emulsifiers, rheology modifiers, preservatives, and the like, to provide the composition with physical properties conducive to ease of manufacture, handling, and formulation, as well as to promote stability of the active substances. Preferably, the composition of the invention is administered on a regular dosage schedule to maintain certain plasma concentrations of lycopene and alpha-tocopherol, for example, on a weekly or daily, or twice daily dosage schedule. The composition of the invention may likewise be administered in a convenient sustained release formulation, which formulations are well-known in the art.

As noted above, lycopene is a naturally-occurring carotenoid found in, for example, tomatoes. Methods of extracting and purifying lycopene from tomatoes are described in, for example, U.S. Pat. Nos. 5,897,866; 5,871,574; 5,858, 700; and 5,836,311, the entire disclosures of which are incorporated herein by reference. Methods for increasing lycopene yields from tomatoes by genetic modification are known and are disclosed in, for example, U.S. Pat. No. 5,304,478, the entire disclosure of which is incorporated herein by reference. Lycopene also can be expressed from other host organisms in accordance with the teachings of U.S. Pat. Nos. 5,837,311; 5,304,978; 5,530,189; 5,429,939; and 5,792,903 the entire disclosures of which are incorporated herein by reference, Alternately, lycopene and its derivatives can be chemically synthesized by methods exemplified by the disclosure of U.S. Pat. No. 5,208,381, the disclosure of which is incorporated herein by reference.

Alpha-tocopherol can be prepared synthetically, although in commercial synthetic preparations the product is always present in admixture with its L-homologue as racemic DL-alpha-tocopherol, which according to present nomenclature is designated as all-rac-alpha-tocopherol, and is a mixture of 8 stereoisomers.

The naturally occurring tocopherols are generally isolated from natural products such as vegetable oil sources by various combinations of such procedures as esterification, saponification, extraction, distillation, ion-exchange, adsorption chromatography, precipitation of sterols, crystallization, and many others. The tocopherol concentrate isolated in this manner will vary depending on the particular vegetable source and separation techniques used. Generally however, the concentrate is a mixture of tocopherol homologues containing about 40% or more impurities such as residual sterols, hydrocarbons, and fatty acids. This concentrate containing up to about 60% mixed tocopherol homologues is suitable for further processing to produce D-alpha-tocopherol of 90% or greater purity.

The non-alpha-tocopherols in the mixture can be converted to the more biologically active D-alpha-tocopherol by introducing methyl substituents into the aromatic ring (Tocol ring). A variety of ways are known for achieving this conversion. The methylation can be done by halomethylation, aminomethylation, hydroxy-alkylation or formylation to introduce a methyl functional group followed by reduction to give the methylated tocopherol.

Further diclosure of methods of producing tocopherols and tocopherol derivatives suitable for use in the present invention, e.g., tocopherol succinate, tocopherol acetate, etc., are found in, for example, U.S. Pat. Nos. 5,686,632 and 5,977,282, the entire disclosures of which are incorporated herein by reference.

6. EXAMPLE

6.1 Materials and Methods

Materials

Synthetic lycopene (95%, all E) was from F. Hoffmann-La Roche Ltd. (Basel, Switzerland), DL-alpha-tocopherol and DL-$\beta$-tocopherol were from Merck KGaA (Darmstadt, Germany), L-ascorbic acid and probucol were from Sigma Chemie (Switzerland), Tetrahydrofuran (THF) containing 0.0025% di-t-butyl-p-cresol as stabilizer was from Fluke Chemie (Buchs, Switzerland) and was used as a solvent for the lycopene. At the tested concentrations (maximal 0.5%), THF was without effect on cell viability.

Carotenoid Solutions

Crystalline lycopene was maintained at −20° C. and fresh 2 mM solutions in THF were prepared under dark room conditions just before the start of the experiments and added at the desired concentrations to the culture medium under vigorous stirring. Final concentrations of lycopene in the medium were determined spectrophotometrically after its extraction with 2-propanol and n-hexane. Dichloromethane (4), alpha-tocopherol, $\beta$-tocopherol and probucol were added as ethanol solutions (final ethanol concentration: 0.1%), and ascorbic acid was added as an aqueous solution.

Cells

Culture media and antibiotics were from Gibco (Grand Island, N.Y., USA). Fetal calf serum was from PAA Labor (Linz, Austria), Human prostate carcinoma, androgen insensitive, cell lines DU-145 and PC-3, colon carcinoma cell line Caco-2, hepatoma cell line HepG2, and rat aortic smooth muscle cell line A7r5 were from American Type Culture Collection (Rockville, Md., USA). DU-146 cells were grown in minimum essential medium (EM), PC-3 cells in F-12K medium, both containing antibiotics and 10% fetal calf serum (FCS). Caco-2 cells were grown in MEM containing 20% FCS. HepG2 cells were grown in MEM containing 10% FCS, and A7r5 cells were grown in DMEM containing 10% FCS.

Cell Proliferation Assay

Cell proliferation was assayed using two methods, cell count and thymidine incorporation:

Cell count. Cells were seeded into 6-multiwell plates (20,000 cells/well). When cells reached approximately 50% confluence, the indicated concentrations of the compounds were added. THF was added to control cells to account for the effect of the solvent in the compound solutions. Cells were washed, trypsinized, resuspended and counted in duplicate at the indicated times by trypan blue dye exclusion with a hemocytometer. Cells that had been passaged between 5 and 20 times were used for all the experiments.

Thymidine incorporation. Colon carcinoma cells (Caco-2) and hepatoma cells (HepG2) seeded into 6 multiwell plates (30,000 cells/well) after treatment were pulsed with [$^3$H] thymidine (0.5 $\mu$Ci per well) for two hours. After labeling, cells were washed with PBS, 0.5% BSA+1% glucose, fixed for 20 minutes with ice-cold 5% trichloracetic acid and solubilized in 0.1 M NaOH/2% Na$_2$CO$_3$/1% SDS. The radioactivity incorporated into the acid-insoluble material was determined in a liquid scintillation analyzer.

6.2 Results

TABLE 1

Effect of Different Concentrations of Lycopene and 50 $\mu$M Alpha-Tocopherol on the Proliferation of Different Types of Cell Lines.

| Cell Line | Lycopene Concentration $\mu$M | | | | |
|---|---|---|---|---|---|
| | 0 | 0.1 | 0.2 | 0.5 | 1 |
| DU 145 | 40 ± 6 | 37 ± 4 | 58 ± 6 | 74 ± 9 | 88 ± 8 |
| HepG2 | 5 ± 1 | 6 ± 1 | 18 ± 3 | 22 ± 4 | 24 ± 4 |
| Caco-2 | 25 ± 3 | 18 ± 3 | 26 ± 5 | 33 ± 2 | 35 ± 3 |
| A7r5 | 40 ± 5 | 14 ± 2 | 28 ± 3 | 37 ± 4 | 41 ± 2 |

The values in Table 1 are expressed as percent of inhibition of proliferation as compared to proliferation of control cells treated with solvent alone. Prostate cancer cells (DU-145), hepatoma cells (HepG2), colon carcinoma cells (Caco-2) and rat aortic smooth muscle cells (A7r5) were treated with different concentrations of lycopene as indicated and 50 $\mu$M alpha-tocopherol for 24 hours. The inhibition in the absence of lycopene ("0" value) is produced by the presence of 50 $\mu$M alpha-tocopherol. Proliferation was assessed as indicated in the Materials and Methods. Data are means±SD of five experiments in duplicate.

In FIG. 1, the effect of lycopene plus alpha-tocopherol on proliferation of DU-145 (A) and PC03 (B) cells is shown. Cells were grown in media containing the indicated concentrations of lycopene plus 50 $\mu$M alpha-tocopherol and compared with cells treated with solvent alone. Proliferation was measured after 12 hour incubation and values were expressed as percentages of the proliferation of control, untreated cells. Results are means±SD of three independent experiments.

In FIG. 2, (A) the effect of the combination of 50 $\mu$M alpha-tocopherol and increasing concentrations of lycopene on DU-145 cell proliferation and (B) the calculated degree of synergism of lycopene and alpha-tocopherol as a function of lycopene concentration are shown. DU-145 cells, in exponentially sowing phase, were treated with indicated concentrations of lycopene alone (square symbols) or with the combination of 50 $\mu$M alpha-tocopherol and lycopene at the indicated concentrations. The expected inhibition value (as expected from the additive effect of the lycopene alone and alpha-tocopherol alone on inhibition of cell proliferation) and the obtained inhibition values for the combination of lycopene and alpha-tocopherol are represented as triangles and circles, respectively. Proliferation was measured as described in Materials and Methods. Percent inhibition is the cell proliferation obtained in treated cells relative to untreated cells taken as control. Percent synergism is the difference in the actual percent inhibition observed with the lycopene and alpha-tocopherol and the values expected from the additive effect of lycopene and alpha-tocopherol. Values are means±SD of five independent experiments.

In FIG. 3, (A) the effect of the concomitant addition of 50 $\mu$M alpha-tocopherol, $\beta$-tocopherol, probucol, or ascorbic acid with 1 $\mu$M lycopene on DU-145 cell proliferation and (B) the calculated degree of synergism between lycopene and the indicated compounds are shown. DU-145 cells were treated either with lycopene alone (empty bars) or with the indicated compounds (hatched bars) or with the combination of the indicated compound plus lycopene (cross-hatched bars). Cell proliferation was determined as described in Materials and Methods. Results are means±SD from a representative three separate experiments.

The data presented herein demonstrate that alpha-tocopherol potentiates the anti-proliferative effect of lycopene and that this effect is specific to alpha-tocopherol as compared to other anti-oxidants, such as $\beta$-tocopherol, probucol and ascorbic acid. The synergy of alpha-tocopherol with lycopene on the inhibition of cell proliferation was particularly pronounced in prostate cancer cells but was also observed in colon and liver cancer cells.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims.

Various references are cited herein, the disclosures of which are incorporated by reference in their entireties.

I claim:

1. A method of treating cancers sensitive to the combination of lycopene and alpha-tocopherol comprising administering to a mammal in need of such treatment an amount of a composition comprising lycopene and alpha-tocopherol, said amount being effective to treat said cancer and wherein the combination effect is greater than the additive effects of lycopene and alpha-tocopherol.

2. The method according to claim 1, in which said amount of said composition is effective to inhibit prostate, liver, or colon carcinoma cell proliferation in the mammal.

3. The method according to claim 1, wherein said administration results in a lycopene plasma concentration of 0.01 to 5.0 $\mu$M and an alpha-tocopherol plasma concentration of 1 to 100 $\mu$M.

4. The method according to claim 3, wherein the lycopene plasma concentration is 0.1 to 1.0 $\mu$M and the alpha-tocopherol plasma concentration is 10 to 100 $\mu$M.

5. The method according to claim 4, wherein the lycopene plasma concentration is 0.1 to 0.75 $\mu$M and the alpha-tocopherol plasma concentration is 25 to 75 $\mu$M.

6. The method according to claim 1 in which said cancer is prostate cancer.

7. The method according to claim 1 in which said mammal is a human.

8. A method of preventing cancers sensitive to the combination of lycopene and alpha-tocopherol in a mammal in need thereof comprising administering to said mammal an amount of a composition comprising lycopene and alpha-tocopherol, said amount being effective to prevent said cancer and wherein the combination effect is greater than the additive effects of lycopene and alpha-tocopherol.

9. The method according to claim 8 in which said amount of said composition is effective to prevent prostate cancer cell, liver cancer cell or colon carcinoma cell proliferation in the mammal.

10. The method according to claim 8, wherein said administration results in a lycopene plasma concentration of 0.01 to 5.0 $\mu$M and alpha-tocopherol plasma concentration of 1 to 100 $\mu$M.

11. The method according to claim 10, wherein the lycopene plasma concentration is 0.1 to 1.0 $\mu$M and the alpha-tocopherol plasma concentration is 10 to 100 $\mu$M.

12. The method according to claim 11, wherein the lycopene plasma concentration is 0.1 to 0.75 $\mu$M and the alpha-tocopherol plasma concentration is 25 to 75 $\mu$M.

13. The method according to claim 8 in which said mammal is predisposed to cancer.

14. The method according to claim 8 in which said cancer is prostate cancer.

15. The method according to claim 8 in which said mammal is a human.

* * * * *